(12) United States Patent
Clemetson

(10) Patent No.: US 8,198,030 B2
(45) Date of Patent: Jun. 12, 2012

(54) RECOMBINANT PLATELET COLLAGEN RECEPTOR GLYCOPROTEIN VI AND ITS PHARMACEUTICAL USE

(75) Inventor: Kenneth J. Clemetson, Bern (CH)

(73) Assignee: Aventis Pharma Deutschland, GmbH, Frankfurt am Main (DE)

( * ) Notice: Subject to any disclaimer, the term of this patent is extended or adjusted under 35 U.S.C. 154(b) by 332 days.

(21) Appl. No.: 11/689,385

(22) Filed: Mar. 21, 2007

(65) Prior Publication Data

US 2007/0172893 A1 Jul. 26, 2007

Related U.S. Application Data

(63) Continuation-in-part of application No. 09/959,802, filed as application No. PCT/EP00/03683 on Apr. 25, 2000, now Pat. No. 7,928,066.

(30) Foreign Application Priority Data

May 7, 1999 (EP) ..................................... 99109094

(51) Int. Cl.
G01N 33/53 (2006.01)
(52) U.S. Cl. ........................................................ 435/7.1
(58) Field of Classification Search .................. None
See application file for complete search history.

(56) References Cited

U.S. PATENT DOCUMENTS

| | | | |
|---|---|---|---|
| 6,245,527 B1 | 6/2001 | Busfield et al. | |
| 6,383,779 B1 | 5/2002 | Busfield et al. | |
| 7,291,714 B1 | 11/2007 | Busfield et al. | |
| 2004/0001826 A1 | 1/2004 | Gill et al. | |
| 2004/0253236 A1 | 12/2004 | Gill et al. | |

FOREIGN PATENT DOCUMENTS

| | | | |
|---|---|---|---|
| WO | WO 95/01375 | | 1/1995 |
| WO | WO 95/11259 A1 | | 4/1995 |
| WO | WO 01/00810 | | 1/2001 |
| WO | WO 02/080968 | | 10/2002 |
| WO | WO 03/008454 | | 1/2003 |
| WO | WO 03/008454 A2 * | | 1/2003 |
| WO | WO 2005/054294 | | 6/2005 |

OTHER PUBLICATIONS

Gibbons Jonathon M. et al.: "Glycoprotein VI is the collagen receptor in platelets which underlies tyrosine phosphorylation of the Fc receptor gamma-chain." FEBS Letters, vol. 413 No. 2, 1997, pp. 255-259.
Jandrot-Perrus Martine et al.: "Adhesion and activation of human platelets induced by convulxin involve glycoprotein VI and integrin alpha-2-beta-1." Journal of Biological Chemistry, vol. 272, No. 43, 1997, pp. 27035-27041.
Gibbons Jonathon M. et al.: << The p85 subunit of phosphatidylinositol 3-kinase associated with the Fc receptor gamma-chain and linker for activator of T cells (LAT) in platelets stimulated by collagen and convulxin. Journal of Biological Chemistry, vol. 273, No. 51, Dec. 18, 1998, pp. 34437-34443.
Clemetson Jeannine et al.: "The platelet collagen receptor glycoprotein VI is a member of the immunoglobulin superfamily closely related to FcalphaR and the natural killer receptors." Journal of Biological Chemistry, vol. 274, No. 41, Oct. 8, 1999, pp. 29019-29024.
Miura Y.: "Platelet Glycoprotein VI" EMBL Database, Accession No. AB035073, Jan. 14, 2000.
Ishibashi et al. International Journal of Hematology 62: 107-115, 1995.
Chiang, Thomas M. et al.: "The signal transduction pathway of the nonintegrin recetor of 65 kDa is different from glycoprotein VI" Archives of Biochemistry and Biophysics 407 (2002) 10-14.
Chiang, Thomas M. et al.: "The Cloning Characterization, and Functional Studies of a Nonintegrin Platelet Receptor for Type I Collagen" The Journal of Clinical Investigations, vol. 100, No. 3, Aug. 1997, 514-521.
Ezumi, Yasuharu et al.: "Molecular Cloning, Genomic Structure, Chromosomal Localization, and Alternative Splice Forms of the Platelet Collagen Receptor Glycoprotein VI" Biochemical and Biophysical Communications 277, 27-36 (2000).
Barrett et al., "Future Innovations in Anti-platelet Therapies", British Journal of Pharmacology 2008, vol. 154, pp. 918-939.
Combe et al, Journal of Thrombosis and Haemostasis, vol. 5, Supplemental 1, Aug. 2007, (Abstract).
Nieswandt et al., "Long-term Antithrombotic Protection by In Vivo Depletion of Platelet Glycoprotein VI in Mice", J. Exp. Med, vol. 193, No. 4, Feb. 19, 2001, pp. 459-469.
Alberio, L. et al., "Collagen Response and Glycoprotein VI Function Decline Progressively as Canine Platelets Age in vivo", Thromb. Haemost, Sep. 2002, vol. 88, No. 3, 510-516.
Apte, A. N. et al., "Anchor-ligated cDNA libraries: A technique for generating a cDNA library for the immediate cloning of the 5' encs of mRNAs," Biotechniques, vol. 15, No. 5, 1993, pp. 890-893 (Abstract Only).
Chiang, T. M. et al., "The signal transduction pathway of the nonintegrin receptor of 65 kDa is different from glycoprotein VI," Archives of Biochemistry and Biophysics, 2002, vol. 407, pp. 10-14.
Chiang, T. M. et al., "Cloning, Characterization, and Functional Studies of a Nonintegrin Platelet Receptor for Type I Collagen" The Journal of Clinical Investigation, Aug. 1997, vol. 100, No. 3, pp. 514-521.

(Continued)

Primary Examiner — Marianne P Allen
(74) Attorney, Agent, or Firm — Millen, White, Zelano, Branigan, P.C.

(57) ABSTRACT

The invention relates to Glycoprotein VI (GPVI), its isolation, purification, and methods for recombinant production. Especially, the invention relates to the use of GPVI, preferably recombinant GPVI, in the treatment of disorders and pathological events correlated directly or indirectly to blood coagulation disorders such as thrombotic and cardiovascular diseases. The extracellular recombinant protein can also be used for establishing screening assays to find potential inhibitors of the membrane bound GPVI in order to inhibit binding of thrombocytes and platelets, respectively, to collagen. Changes in GPIV can be used to monitor platelet age and exposure to thrombotic and cardiovascular diseases.

2 Claims, 2 Drawing Sheets

OTHER PUBLICATIONS

Ezumi, Y. et al., "Molecular Cloning, Genomic Structure, Chromosomal Localization, and Alternative Splice Forms of the Platelet Collagen Receptor Glycoprotein VI" Biochemical and Biophysical Communications, vol. 277, 2000, pp. 27-36.

Ezumi, Y. et al., "Physical and Functional Association of the Src Family Kinases Fyn and Lyn with the Collagen Receptor Glycoprotein VI-Fc Receptor Chain Complex on Human Platelets," J. Exp. Med., Jul. 20, 1998, vol. 188, No. 2, pp. 267-276.

Gruner, S. et al., "Anti-Glycoprotein VI Treatment Severely Compromises Hemostasis in Mice With Reduced $\alpha 2\beta 1$ Levels or Concomitant Aspirin Therapy" Circulation, 2004, vol. 110, pp. 2946-2951.

Hickey et al., "Human platelet glycoprotein IX: An adhesive prototype of leucine-rich glycoprotein with flank-center-flank structures," Proc. Natl. Acad. Sci., Sep. 1989, vol. 86, pp. 6773-6777.

Jandrot-Perrus, M. et al., "Cloning, characterization, and functional studies of human and mouse glycoprotein VI: a platelet-specific collagen receptor from the immunoglobulin superfamily," Blood, Sep. 1, 2000, vol. 96, No. 5, pp. 1798-1807.

Jin, J. et al., "Molecular Basis for ADP-induced Platelet Activation" The Journal of Biological Chemistry, Jan. 23, 1998, vol. 273, No. 4, pp. 2030-2034.

Knight, C. G. et al., "Collagen-platelet interaction: Gly-Pro-Hyp is uniquely specific for platelet1 Gp VI and mediates platelet activation by collagen." Cardiovascular Research, 1999, vol. 41, pp. 450-457.

Massberg et al., "Soluble Glycoprotein VI Dimer Inhibits Platelet Adhesion and Aggregation to the Injured Vessel Wall in vivo", The Faseb Journal, Feb. 2004, vol. 18, pp. 397-399.

Miura, Y. et al., "Analysis of the Interaction of Platelet Collagen Receptor Glycoprotein VI (GPVI) with Collagen" The Journal of Biological Chemistry, 2002, vol. 277, No. 48, pp. 46197-46204.

Miura, Y. et al., "Cloning and Expression of the Platelet-Specific Collagen Receptor Glycoprotein VI" Thrombosis Research, 2000, vol. 98, pp. 301-309.

Nieswandt, B. et al., "Long-term Antithrombotic Protection by In Vivo Depletion of Platelet Glycoprotein VI in Mice," J. Exp. Med., Feb. 19, 2001, vol. 193, No. 4, pp. 459-469.

Wicki, A. N. et al., "Isolation and Characterization of Human Blood Platelet mRNA and Contstruction of a cDNA Library in $\lambda$gt11," Thrombosis and Haemostasis, 1989, vol. 61, pp. 448-453.

BigLake, B. et al., "Glycoprotein VI as a prognostic biomarker for cardiovascular death in patients with symptomatic coronary artery disease," Clin. Res. Cardiol., 2010, vol. 99, pp. 227-233.

BigLake, B. et al., "Diagnostic and therapeutic potentials of platelet glycoprotein VI," Seminars in Thrompbosis and Hemostasis, 2010, vol. 38, No. 2, pp. 203-211.

Heemskerk, J. W. M. et al., "Functional of glycoprotein IV and integrin alpha2beta1 in the procoagulant response of single, collagen-adherent platelets," Thrombosis and Haemostasis, May 1, 1999, vol. 81, No. 5, pp. 782-792.

Ichinohe, T. et al., "Cyclic AMP-insensitive activation of c-Src and Syk protein-tyrosine kinases through platelet membrane glycoprotein VI.," The Journal of Biological Chemistry, Nov. 24, 1995, vol. 270, No. 47, pp. 28029-28036.

Sugiyama, T. et al., "A novel platelet aggregating factor found in a patient with defective collagen-induced platelet aggregation and autoimmune thrombocytopenia," Blood, Jun. 1, 1987, vol. 69, No. 6, pp. 1712-1720.

Sugiyama, T. et al., "Functional role of the antigen recognized by an antiplatelet antibody specific for a putative collagen receptor in platelet collagen interaction," International Journal of Hematology, Aug. 1993, vol. 58, No. 1-2, pp. 99-104.

\* cited by examiner

Figure 1.

(1a)
```
1                    20
MSPSPTALFC LGLCLGRVPA
```

(1b)
```
1
QSGPLPKPSL QALPSSLVPL EKPVTLRCQG PPGVDLYRLE KLSSSRYQDQ  (50)

AVLFIPAMKR SLAGRYRCSY QN*GSLWSLPS DQLELVATGV FAKPSLSAQP  (100)

GPAVSSGGDV TLQCQTRYGF DQFALYKEGD PAPYKNPERW YRASFPIITV  (150)

TAAHSGTYRC YSFSSRDPYL WSAPSDPLEL VVTGTSVTPS RLPTEPPSSV  (200)

AEFSEATAEL TVSFTNKVFT TETSRSITTS PKESDSPAGP ARQYYTKGNL  (250)

VRICLGAVIL IILAGFLAED WHSRRKRLRH RGRAVQRPLP PLPPLPQTRK  (300)

SHGGQDGGRQ DVHSRGLCS  (319)
```

Figure 2:

```
GAGCTCAGGA CAGGGCTGAG GAACCATGTC TCCATCCCCG ACCGCCCTCT (50)

TCTGTCTTGG GCTGTGTCTG GGGCGTGTGC CAGCGCAGAG TGGACCGCTC (100)

CCCAAGCCCT CCCTCCAGGC TCTGCCCAGC TCCCTGGTGC CCCTGGAGAA

GCCAGTGACC CTCCGGTGCC AGGGACCTCC GGGCGTGGAC CTGTACCGCC (200)

TGGAGAAGCT GAGTTCCAGC AGGTACCAGG ATCAGGCAGT CCTCTTCATC

CCGGCCATGA AGAGAAGTCT GGCTGGACGC TACCGCTGCT CCTACCAGAA (300)

CGGAAGCCTC TGGTCCCTGC CAGCGACCA GCTGGAGCTC GTTGCCACGG

GAGTTTTTGC CAAACCCTCG CTCTCAGCCC AGCCCGGCCC GGCGGTGTCG (400)

TCAGGAGGGG ACGTAACCCT ACAGTGTCAG ACTCGGTATG GCTTTGACCA

ATTTGCTCTG TACAAGGAAG GGGACCCTGC GCCCTACAAG AATCCCGAGA (500)

GATGGTACCG GGCTAGTTTC CCCATCATCA CGGTGACCGC CGCCCACAGC

GGAACCTACC GATGCTACAG CTTCTCCAGC AGGGACCCAT ACCTGTGGTC (600)

GGCCCCCAGC GACCCCCTGG AGCTTGTGGT CACAGGAACC TCTGTGACCC

CCAGCCGGTT ACCAACAGAA CCACCTTCCT CGGTAGCAGA ATTCTCAGAA (700)

GCCACCGCTG AACTGACCGT CTCATTCACA AACAAAGTCT TCACAACTGA

GACTTCTAGG AGTATCACCA CCAGTCCAAA GGAGTCAGAC TCTCCAGCTG (800)

GTCCTGCCCG CCAGTACTAC ACCAAGGGCA ACCTGGTCCG GATATGCCTC

GGGGCTGTGA TCCTAATAAT CCTGGCGGGG TTTCTGGCAG AGGACTGGCA (900)

CAGCCGGAGG AAGCGCCTGC GGCACAGGGG CAGGGCTGTG CAGAGGCCGC

TTCCGCCCCT GCCGCCCCTC CCGCAGACCC GGAAATCACA CGGGGGTCAG (1000)

GATGGAGGCC GACAGGATGT TCACAGCCGC GGGTTATGTT CATGACCGCT

GAACCCCAGG CACGGTCGTA TCCAAGGGAG GGATCATGGC ATGGGAGGCG (1100)

ACTCAAAGAC TGGCGTGTGT GGAGCGTGGA AGCAGGAGGG CAGAGGCTAC

AGCTGTGGAA ACGAGGCCAT GCTGCCTCCT CCTGGTGTTC CATCAGGGAG (1200)

CCGTTCGGCC AGTGTCTGTC TGTCTGTCTG CCTCTCTGTC TGAGGGCAC (1249)
```

RECOMBINANT PLATELET COLLAGEN RECEPTOR GLYCOPROTEIN VI AND ITS PHARMACEUTICAL USE

This application is a continuation-in-part divisional application of U.S. Ser. No. 09/959,802, filed Nov. 7, 2001 now U.S. Pat. No 7,928,066, which is a U.S. National Stage 371 application based on PCT/EP00/03683, filed Apr. 25, 2000, both of which are incorporated by reference herein.

The invention relates to Glycoprotein VI (GPVI), its isolation, purification, and methods for recombinant production. Especially, the invention relates to the use of GPVI, preferably recombinant GPVI, in the treatment of disorders and pathological events correlated directly or indirectly to blood coagulation disorders such as thrombotic and cardiovascular diseases. The extracellular recombinant protein can also be used for establishing screening assays to find potential inhibitors of the membrane bound GPVI in order to inhibit interaction of platelets and collagen. GPVI on the platelet surface is modified during the platelet lifetime in vivo and can therefore be used as a marker of the platelet age profile.

Glycoprotein VI is a 62/65 kDa (non-reduced/reduced respectively) platelet membrane glycoprotein which forms a complex together with the Fcγ common subunit. The GPVI subunit contains the collagen binding site and the Fcγ subunit is responsible for signaling. The complex forms one of the major collagen receptors on the platelet surface, critical for platelet activation in response to collagen. The recognition sequence on collagen consists of $(GlyProHyp)_n$ sequences. Patients are known from Japan who have a genetic deficiency of GPVI. They have mild bleeding problems and their platelets respond only weakly to collagen, presumably via other receptors. A great deal has been learned about the signaling cascades originating at GPVI which strongly resemble those from immune receptors including T-cell receptors, B-cell receptors and natural killer cell receptors. These cascades involve src family tyrosine kinases such as Fyn and Lyn as well as $p72^{SYK}$ and many other tyrosine kinases and phosphatases and adaptor proteins such as LAT. A main target of these cascades is activation of phospholipase Cγ2 which splits phospholipids to give the second messengers diacylglycerol and $IP_3$. GPVI is thought to be involved in activation of the platelet integrin α2β1 which has a major role in platelet adhesion to damaged vessel wall. Mice with the Fcγ subunit "knocked-out" have platelets which still show responses to collagen implying that the resting state of α2β1 may also be regulated by the GPVI/Fcγ complex.

The platelet collagen receptor GPVI is closely related to the natural killer activatory receptors of the p58KAR family as well as to FcαR.

The adhesion and activation of resting, circulating platelets at a site of vascular injury is the first step in a process leading to the formation of a thrombus which is converted into a haemostatic plug. Collagen is one of the major components of the vessel wall responsible for platelet activation. Many types of collagen exist and seven of these are found in the subendothelial layers. Several different receptors for collagen have been identified on platelets but the major ones are now considered to be the integrin $α_2β_1$ and the non-integrin GPVI. Although $α_2β_1$ is well characterised and both subunits were cloned and sequenced several years ago, the structure of GPVI has remained elusive although several features have been identified. It was determined about twenty years ago that GPVI is a major platelet glycoprotein with a molecular mass in the 60-65 kDa range and an acid pI. Its role as a putative collagen receptor was established following the identification of a patient in Japan with a mild bleeding disorder whose platelets showed a specific defect of response to collagen and lacked this receptor. This patient had also developed autoantibodies to the deficient receptor and these were used to characterise the molecule further. More recently it was established that GPVI is associated non-covalently with the common Fcγ subunit which acts as the signaling part of the complex. It was also demonstrated that the recognition sequence on collagen for GPVI is a repeated Gly-Pro-Hyp triplet within the collagen triple helical structure and that synthetic peptides based on this structure could be used as specific GPVI directed agonists. The GPVI/Fcγ complex was shown to signal to the platelet interior by an immune receptor-like mechanism, involving activation of $p72^{SYK}$ and leading by a cascade of kinase/phosphatase/adaptor protein interactions to activation of PLCγ2 and hence to release of granules and platelet aggregation. A further step in characterisation of this molecule was the demonstration that the snake C-type lectin, convulxin, from the Tropical Rattlesnake, *Crotalus durissus terrificus* was able to activate platelets by clustering GPVI through a multimeric interaction. Convuxin was shown to bind specifically to GPVI providing a method for purification of this receptor in conjunction with established approaches.

Thus, it is clear from the prior art that GPVI seems to be a very interesting compound in many therapeutical fields above all concerning with applications which are related, directly or indirectly, to blood coagulation events which depend on collagen—platelet interaction. It was, therefore, the goal of the present invention is to provide GPVI in a recombinant form and to show its efficiency as direct therapeutical target or as tool for screening of short compounds, especially chemically synthesized or synthesizable compounds having the capability to inhibit or block the natural platelet-collagen interaction.

The invention relates also to portions or fragments of the GPVI protein which have maintained their biological activity which is the binding to collagen.

The invention was successful in purifying adequate amounts of GPVI for preliminary characterisation and for peptide sequencing. The sequences were used to design primers for PCR to identify a positive sequence in a DNA library. This DNA sequence was then used as a probe to isolate an almost complete cDNA sequence from the library and missing 5'-sequence was obtained using a RACE method from a platelet cDNA library.

The invention was also successful in showing the use of recombinant GPVI as therapeutically applicable compound which is capable, when administered in a patient with e.g. damaged blood vessels, to bind to collagen, thus preventing platelets bearing membrane-bound GPVI from binding to said collagen. The recombinant soluble extracellular domain of GPVI contains the collagen binding site and can prevent platelet activation by collagen. It could therefore be applicable to treatment of disease conditions involving increased platelet activation with collagen, such as atherosclerotic plaque rupture, in diseases such as unstable angina or, during surgical treatment such as Percutaneous Transluminal Coronary Angioplasty (PTCA), where arteries are reopened by inflation of a balloon catheter causing considerable damage to the vessel wall and much platelet activation and often resulting in reclosure of the vessel later. The advantage of recombinant GPVI fragments compared to present treatment methods is that they act at an earlier stage by preventing or reducing platelet activation rather than by suppressing events after platelet activation, such as aggregation by GPIIb-IIIa antagonists. Thus, smaller amounts of platelet granule contents are released including growth factors and chemokines which are involved not only in wound repair but in the remodelling of the vessel wall by smooth muscle migration and in attraction of phagocytic cells such as monocytes known to contribute to atherosclerosis. Fab fragment of humanised mouse monoclonal antibodies against GPVI could be used with similar effect to block GPVI on the platelet surface with similar applications as above.

Recombinant GPVI according to this invention can also be used in a binding assay to collagen to screen for small molecules (in combinatory libraries for example) capable of inhibiting this interaction and which can be used to develop therapeutic compounds which are inhibitors of the collagen-platelet interaction.

By suitable derivatisation these compounds are made orally available. Again the main objective is to prepare compounds reducing GPVI-collagen interactions and hence platelet activation in situations where platelets come into contact with collagen. The screening technology as such used in this invention is well established in the prior art. By such screening assays the invention enables finding and developing new targets which can inhibit the natural membrane-bound GPVI on the platelet surface as a collagen antagonist. Such targets which may be small chemical molecules may then be the basis for further inventions.

Another major application of GPVI and reagents that recognize specific domains of GPVI is as markers of platelet age and functionality. Young platelets are generally thought to be more active and functional than older ones. Young platelets bind to and are activated by the snake venom C-type lectin convulxin, which is specific for GPVI, and as they age both the binding and degree of activation decrease. This can be due to either proteolytic or conformational changes in GPVI or its association with Fcγ due to platelet activation or damage in the circulation. This can be a useful parameter to measure the age and function profile of platelets in patients as well as in normal persons during medical controls. The platelet age profile changes in many diseases affecting the bone marrow or the immune system and could be an important diagnostic criterion if better methods for its determination were available. For example, patients with diseases involving increased platelet turnover will show more young platelets whereas patients on chemotherapy or radiation treatment will show a steadily aging population. Thus, such an age profile can be used for a precise monitoring of treatment. In a normal healthy population very little is known about the age profile distribution and its role as a predictor of changes in health. It is not known whether the changes in GPVI are due to the partial involvement of platelets in haemostatic events and whether changes might be more pronounced in patients with extensive cardiovascular disease. At present thiazole orange is used to detect young reticulated platelets containing mRNA. This mRNA soon decays, restricting the method to only the youngest platelets. Reagents which could be used in such an assay would include GPVI-specific snake venom proteins such as convulxin, or monoclonal or polygonal antibodies recognising the N-terminal region of GPVI or monoclonal antibodies recognising new sites or conformations exposed by proteolysis of the N-terminal domain or specific conformations is present either in the intact molecule and not in the aged one or vice versa or small chemical entities selected to recognise specifically intact GPVI or its modified form. These reagents would be labeled with a fluorescent marker, or together with a fluorescent labeled second antibody or affinity reagent and used in flow cytometry to measure the platelet binding profile. At a later stage alternative, less labour intensive measuring techniques based on automated measuring of platelet profiles could be adopted. Using cell sorting methods with flow cytometry or magnetic beads it should be possible to isolate young and old platelets to examine the factors involved in removal of old platelets from the circulation. Reagents recognizing specific forms of GPVI would be a key to such studies.

Therefore, it is an object of the present invention to provide a DNA coding for Glycoprotein VI or biological active fragments thereof, especially the sequence of FIG. 2.

It is a further object of this invention to provide a DNA coding for Glycoprotein VI comprising the amino acid sequences of FIGS. 1a and 1b.

It is another object of this invention to provide a pharmaceutical composition comprising recombinant GPVI together with a pharmaceutically acceptable diluent, carrier or excipient, and its use for the manufacture of a medicament in the therapeutical field of thrombotic and cardiovascular events and disorders related to platelet-collagen interactions Another object of the invention is the use of recombinant GPVI in a screening tool for detecting specific inhibitors of platelet-collagen interactions.

Another object of the invention is the use of GPVI as a marker for platelet age and exposure to cardiovascular diseases.

Possible medical indications and applications, respectively, are, for example, unstable angina pectoris, PTCA, use of stents in this field, operations on coronary vessels, general operations on blood vessels, operations which may damage larger blood vessels such as hip joint operations. Moreover, all indications are included which relate to thromboembolic events caused by disorders of the interaction between the vessel wall and the coagulation system with a high risk of formation of thrombi and blocking of vessels.

As indicated above, the GPVI protein and fragments thereof according to the present invention are suitable as pharmaceutically effective compounds in pharmaceutical compositions and combinations.

The pharmaceutical formulations according to the invention optionally may comprise additional active ingredients like anti-coagulants such as hirudin or heparin or thrombolytic agents such as plasminogen activator or hementin or antagonists to other platelet receptors such as GPIIb-IIIa antagonists like abciximab or eptifibatide or ADP-receptor antagonists such as clopidogrel.

The novel protein, and its biological active fragments respectively, according to the invention may form pharmaceutically acceptable salts with any non-toxic, organic or inorganic acid. Inorganic acids are, for example, hydrochloric, hydrobromic, sulphuric or phosphoric acid and acid metal salts such as sodium monohydrogen orthophosphate and potassium hydrogen sulfate. Examples for organic acids are the mono, di and tri carboxylic acids such as acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic and sulfonic acids such as methane sulfonic acid. Salts of the carboxy terminal amino acid moiety include the non-toxic carboxylic acid salts formed with any suitable inorganic or organic bases. These salts include, for example, alkali metals such as sodium and potassium, alkaline earth metals such as calcium and magnesium, light metals of Group IIIA including aluminium, and organic primary, secondary and tertiary amines such as trialkylamines, including triethylamine, to procaine, dibenzylamine, 1-ethenamine, N,N'-dibenzylethylene-diamine, dihydroabietylamine and N-alkylpiperidine.

As used herein, the term "pharmaceutically acceptable carrier" means an inert, non toxic solid or liquid filler, diluent or encapsulating material, not reacting adversely with the active compound or with the patient. Suitable, preferably liquid carriers are well known in the art such as sterile water, saline, aqueous dextrose, sugar solutions, ethanol, glycols and oils, including those of petroleum, animal, vegetable, or synthetic origin, for example, peanut oil, soybean oil and mineral oil.

The formulations according to the invention may be administered as unit doses containing conventional non-toxic pharmaceutically acceptable carriers, diluents, adjuvants and vehicles which are typical for parenteral administration.

The term "parenteral" includes herein subcutaneous, intravenous, intra-articular and intratracheal injection and infusion techniques. Also other administrations such as oral administration and topical application are suitable. Parenteral compositions and combinations are most preferably administered intravenously either in a bolus form or as a constant fusion according to known procedures. Tablets and capsules for oral administration contain conventional excipients such as binding agents, fillers, diluents, tableting agents, lubricants, disintegrants, and wetting agents. The tablets may be coated according to methods well known in the art.

Oral liquid preparations may be in the form of aqueous or oily suspensions, solutions, emulsions, syrups or elixirs, or may be presented as a dry product for reconstitution with water or another suitable vehicle before use. Such liquid preparations may contain conventional additives like suspending agents, emulsifying agents, non-aqueous vehicles and preservatives.

Topical applications may be in the form of aqueous or oily suspensions, solutions, emulsions, jellies or preferably emulsion ointments.

Unit doses according to the invention may contain daily required amounts of the protein according to the invention, or sub-multiples thereof to make up the desired dose. The optimum therapeutically acceptable dosage and dose rate for a given patient (mammals, including humans) depends on a variety of factors, such as the activity of the specific active material employed, the age, body weight, general health, sex, diet, time and route of administration, rate of clearance, the object of the treatment, i.e., therapy or prophylaxis and the nature of the thrombotic disease to be treated, antiplatelet or anticoagulant activity.

Therefore, in compositions and combinations useful as anticoagulants in a treated patient (in vivo) a pharmaceutical effective daily dose of the peptides of this invention is between about 0.01 and 100 mg/kg body weight, preferably between 0.1 and 10 mg/kg body weight. According to the application form one single dose may contain between 0.5 and 10 mg of the collagen inhibitor To achieve an anticoagulant effect in extracorporeal blood a pharmaceutically effective amount of the inventive peptides is between 0.2 and 150 mg/l, preferably between 1 mg and 20 mg/l extracorporeal blood.

SHORT DESCRIPTION OF THE FIGURES

FIG. 1: Protein sequence of GPV1 (one-letter-code)
1a: Leader sequence (SEQ ID NO: 2)
1b: Mature protein (SEQ ID NO: 3)
Open reading frame: 339 amino acids
Asterisk: Glycosylation site
Double underline: Transmembrane domain
Underline: Sequenced peptides
FIG. 2: GPVI nucleotide sequence (SEQ ID NO: 1) covering open reading frame of 1017 by plus 3' and 5' regions total 1249 bp

DETAILED DESCRIPTION OF THE INVENTION

Two sequences of 7 amino acids showing the least degeneracy in the genetic code were chosen for the synthesis of DNA primers in order to amplify part of the of GPVI cDNA by PCR. As the location of both peptides in the protein were totally unknown, for each of them, two degenerate primers, one sense and one antisense were prepared. These primers were used to amplify a human bone-marrow library. The combination of the sense 5' TYA THC CNG CNA TGA ARMG 3' (SEQ ID NO: 4) primer coding for the sequence PAMKRSL (SEQ ID NO: 5) with the antisense 5' TTR TAN ARN GCR AAY TGR TC 3' (SEQ ID NO: 6) one corresponding to DQFALYK (SEQ ID NO: 7) amplified a DNA fragment of 221 bp. In addition to the selected peptides, the amplified DNA coded for the LysC/AspN peptide DQLELVATGV-FAKPSLSAQPGPAVSS (SEQ ID NO: 11), clearly linking the sequence to the cDNA for GPVI.

Screening 600.000 pfu from a bone marrow library with this 221 bp DNA fragment produced 4 positive pfu. Three had inserts of 1350 bp whether cut by the restriction enzymes Sal I or EcoR I and belonged to the IgG superfamily. The fourth one had an 4.6 kb insert by Sal I digestion and gave two fragments of 2300 bp and 1300 bp respectively when treated by EcoRI. Its DNA encoded the sequence for the 10 peptides derived from amino acid sequencing of GPVI but stopped short of the amino terminal. No starting methionine or leader sequence could be found but more than 2000 bp of previously sequenced non-reading frame DNA terminating in an Alu sequence were present. The 5' end RACE experiment was completed on platelet poly A RNA with primers located in a part of the GPVI sequence which had been corroborated by that of the peptides. A fragment of 348 bp including 278 bp on the sequence of the fourth clone and 70 bp new from bp 1987 corresponding to 14 amino acids including the first methionine were found before falling back on the established GPVI sequence. Thus, a cDNA containing a total of 1249 bp, a 25 bp 5' sequence upstream of the start codon, an open reading frame of 1017 bp coding for a protein, including leader sequence, with 339 amino acids, and a 3' region of 207 bp including the stop codon could be sequenced.

A cDNA coding for platelet GPVI was cloned and sequenced from a human bone marrow cDNA library using RACE with platelet mRNA to supply missing 5' sequence. The open reading frame of 1017 bp encodes 339 amino acids and a untranslated 3' region. Hydrophobicity analysis of the amino acid sequence revealed the presence of two putative transmembrane domains, a putative 20 amino acid signal sequence, and a 19 amino acid domain between residues 247 and 265 of the mature protein. The sequence and its amino acid translation are shown in FIG. 2 and FIG. 1. A comparison with the amino acid sequence of the most similar molecules found in a search of GenBank reveals clearly that it belongs to the immunoglobulin superfamily and the extracellular domain contains two Ig C2-domain loops formed by two disulphide bridges. It is a membrane crossing protein class one molecule with the N-terminus at the exterior and traverses the membrane once. The most closely related molecules belong to the natural killer receptor class which contains both inhibitory and activatory types. GPVI clearly belongs to the activatory subclass not only through its function but also because unlike the inhibitory class it does not contain ITIM sequences in its cytoplasmic domain. Neither does it contain any tyrosine residues which might be involved in phosphorylation. There are some threonine and serine residues in this domain but they do not match any criteria for kinase consensus sequences. Like the activatory class of NK receptors, GPVI contains an arginine residue as the third amino acid of the membrane crossing domain which is involved in the complex formation with the Fcγ subunit. The cytoplasmic domain contains 51 amino acids, showing only a minor similarity (in the region just below the membrane) to the cytoplasmic domains of other members of this family. This suggests that this domain in GPVI may associate with different types of cytoplasmic molecule than the other family members. GPVI contains only a single putative N-glycosylation site at Asn69. The domain just above the membrane after the beta sheets of the Ig domains finish, however, is rich in theonine and serine residues which could provide O-glycosylation sites such as are found in GPIbα and GPV. The main function of this O-glycosylation seems to be to present the receptor structures well-extended from the platelet surface to facilitate the interactions with their bulky ligands. Since GPVI was earlier established as a sialoglycoprotein, the difference in molecular mass between the theoretical amino acid mass (37 kDa) and the mass determined by gel electrophoresis (65 kDa reduced) must be due to this glycosylation.

The structure of natural killer receptors of the two domain type has been established by X-ray crystallographic studies and the two Ig-domains were shown to form an acute angle with the receptor site for the peptide-carrying HLA antigens lying on the outside of the elbow. A direct comparison of the structure of the HLA peptide binding site with that of collagen immediately suggests why these receptors have a common origin because the multiple alpha-helical structures of the HlA binding site and the peptide it contains strongly resemble the triple helical structure of collagen. The natural killer receptors are postulated to work by a dimerisation mechanism with two receptors recognising two separate HLA sites on the cell which the natural killer cell is investigating. Possibly this dimerisation is part of the activation or deactivation mechanism, depending on the class of receptor. In the case of GPVI there may as well be the possibility for two GPVI molecules to associate with one Fcγ, since each monomer of the Fcγ dimer has a recognition sequence. However, the stoichiometry is not yet known, and based upon the structure of collagens, collagen-like peptides that act via GPVI and convulxin, it seems likely that the strength of the signal is related to the number of GPVI/Fcγ complexes that are clustered together. Other platelet receptors belonging to this Ig family include ICAM-2 (CD102) and PECAM (CD31).

All microorganisms, cell lines, expression systems, expression hosts, plasmids, promoters, resistance markers, replication origins, restriction sites or other fragments or parts of vectors which are mentioned in the description not directly in connection with the claimed invention are commercially or otherwise generally available. Provided that no other hints are given, they are used only as examples and are not essential with respect to the invention, and can be replaced by other suitable tools and biological materials, respectively.

The techniques which are essential according to the invention are described in detail below and above. Other techniques which are not described in detail correspond to known standard methods which are well known to a person skilled in the art, or are described more in detail in the cited references and patent applications and in the standard literature (e.g. Sambrook et al., 1989, Molecular Cloning: A Laboratory Manual, 2nd Edition, Cold Spring Harbor; Harlow, Lane, 1988, Antibodies: A Laboratory Manual, Cold Spring Harbor).

EXAMPLES

Example 1

Materials—Protein A-Sepharose, peroxidase-conjugated goat anti-mouse and anti-rabbit antibodies, bovine serum albumin, *Crotalus durissus terrificus* venom, wheat germ aggulutinin (VGA), N-hydroxysuccinimidyl chloroformate-activated cross-linked 4% beaded agarose and Triton X-114 were from Sigma Chemical Co. (St Louis, Mo.), Octanoyl-N-methyl-glucamide (ONMG) and nonanoyl-N-methyl-glucamide (NNMG) were from Oxyl Chemie (Bobingen, Germany).

Example 2

GPVI isolation from platelets—Membrane glycoproteins were isolated from platelets as previously described. Briefly, platelets (from 40 buffy coats) were washed and lysed in 2% Triton X-114 in the presence of protease inhibitors. The Triton X-114 and aqueous phases were separated and the detergent phase was loaded on a column of wheat-germ agglutinin coupled to Sepharose 4B. The platelet glycoproteins were eluted with 10 mM Tris HCl, pH 7.4, 30 mM NaCl, 0.2% octanoyl-N-methylglucamide (ONMG) and 2% N-acetylglucosamine. After dialysis and concentration, the solution of glycoproteins was loaded on a column of convulxin bound to N-hydroxylsuccinamidyl-p-nitrophenyl chloroformate activated cross-linked 4% beaded agarose (1 mg/ml). The column was washed with 4 volumes of 10 mM Tris HCl, pH7.4, 30 mM NaCl, 0.2% nonanoyl-N-methylglucamide (NNMG), and then with 4 volumes of 10 mM Tris HCl, pH7.4, 30 mM NaCl and 2% NNMG. GPVI was eluted with 0.08% SDS in 10 mM Tris/HCl, pH 7.4. The solution was concentrated and loaded on a preparative gel of 8.5% polyacrylamide using the Model 491 Prep Cell (BioRad, CA). The preparative electrophoresis was performed under non-reduced conditions following the manufacturer instructions. GPVI eluted as a single band at 65 kDa. The fractions were pooled, concentrated on Centricon-30 (Amicon, Beverly, Mass.) and resuspended in 10 mM Tris/HCl, pH7.4 and 0.1% ONMG.

Example 3

Amino acid analysis of GPVI—GPVI was digested with the endoproteinases LysC and AspN (Boehringer Mannheim, Germany). The 10 peptides generated were separated by reverse-phase HPLC and sequenced on an Applied Biosystem model 477A pulsed-liquid-phase protein sequencer with a model 120A on-line phenylthiohydantoin amino acid analyser.

Example 4

Amplification of a 221 bp fragment coding for part of GPVI from a λgt11 cDNA library—

A sample ($10^{10}$ pfu) (plaque forming units) from a human bone marrow library—(Clonetech, Palo Alto, Calif.) was amplified using 2 combinations of 4 degenerate primers. The final primer concentrations were 2 μM, the dNTP concentration was 200 μM and 2 U/110 μl reaction AmpliTaq Gold (Perkin Elmer, Rotkreuz, Switzerland) were used. The PCR conditions were 5 cycles at 37° C. followed by 30 cycles at 44°C. The sense 19mer 5' TYATHCCNGCNATGAARMG 3' (SEQ ID NO: 4) and the antisense 20mer 5' TTR-TANARNGCRMYTGRTC 3' (SEQ ID NO: 6) amplified a 221 bp fragment which was subcloned in Bluescript KS+ (Stratagene, La Jolla, Calif.) and sequenced using the T7 Sequenase kit (Amersham, Switzerland).

Example 5

Screening the λgt11 cDNA library with the 221 bp GPV probe—The 221 bp fragment was cut from the plasmid, cleaned and labeled with α³²P-ATP (20 MBq/50 µl, Hartmann Analytik, Braunschweig, Germany) using the High Prime Labeling kit (Boehringer Mannheim, Switzerland). The human bone marrow library was screened following the manufacturer instructions. Positive phages were grown, their DNA isolated and subcloned in BlueScript using either EcoRI or Sal I sites and sequenced. Sequencing was performed using the ABS system of RACE-Platelet poly A RNA was prepared as previously described (Power et al., Cytokine 7, 479-482, 1995). Reverse transcription (30 µl) was performed using 5 µg of poly A RNA with the primer 5'TGAATGAGACGGTCAGTTCAGC 3' (SEQ ID NO: 8) (20 µM), dNTP (1 mM), RNAsin (40 U), 1×AMV buffer and 20 U AMV reverse transcriptase for 20 min at 45° C. followed by 20 min at 52° C. The reaction mixture was treated with 2 µl 6N NaOH at 65° C. for 30 min, neutralised with 2 µl 6N acetic acid, and concentrated in a Centricon 30 (Amicon). An anchor was ligated to the first strand DNA following the protocol of Aptes and Siebert (BioTechniques 15: 890-893, 1993). Nested PCR was performed using a primer complementary to the anchor and the primer 5' TTGTACAGAGCAAATTGGTC 3' (SEQ ID NO: 9) (35 cycles, 55°C) and followed by the primer 5' GACCAGAGGCTCCGTTCTG 3' (SEQ ID NO: 10) (30 cycles at 53° C.). The highest band (350 bp) was separated by agarose electrophoresis from the lower ones, subcloned into BlueScript, and sequenced.

Example 6

Preparation of anti-GPVI Fab and F(ab)₂—Polyclonal antisera against human GPVI were generated in rabbits. IgG from rabbit anti-GPVI antiserum was purified as described. Digestion of IgG with immobilized papain (Pierce) to generate Fab fragments was performed according to the standard protocol of the supplier. Fab fragments were separated from undigested IgG and Fc fragments using an immobilized Protein A (Sigma) column. The flowthrough was transferred to a dialysis tube, concentrated using solid polyethyleneglycol 20,000, thoroughly dialysed against 20 mM Hepes, 140 mM NaCl, 4 mM KCl, pH 7.4 and stored at 4° C. until used. F(ab')₂ fragments were prepared by pepsin digestion of $I_gG$, 1:50 enzyme to substrate ratio (w/w), in 0.5 M acetate buffer, pH 4.0, at 37° C. for 18 hr. The pH was corrected to 7.4 with diluted NaOH and the sample was dialysed against 20 mM phosphate, pH 7.4. F(ab')₂ fragments were separated from undigested IgG and Fc fragments using Protein A chromatography. The flow-through was transferred to dialysis tube, concentrated using solid polyethyleneglycol 20 000, intensively dialysed against 20 mM Hepes, 140 mM NaCl, 4 mM KCl, pH 7.4 and stored in aliquots at –20° C. Washed platelets were lysed in Triton X-114 and phase separation was performed on the soluble material before isolating the membrane glycoproteins associated with the Triton X-114 phase by affinity chromatography on wheat germ agglutinin-Sepharose 4B as described previously. As GPVI represents a very small fraction of the platelet membrane glycoprotein pool, we used the specificity of the snake C-type lectin convulxin for isolation of this receptor. Affinity chromatography on convulxin coupled to Sepharose 4B yielded a 65 kDa protein as major product.

However, uncharacterized material of both higher and lower Mr co-eluted with GPVI and could not be removed by extensive washing of the column. Preparative gel electrophoresis on 8.5% polyacrylamide was added as a final step of purification. Fractions containing GPVI were pooled and gave a single band on reanalysis. Purified GPVI was tested for its ability to block platelet aggregation by collagen. A slight inhibitory effect was observed when aliquots of GPVI solution were added to the platelet suspension. However, by preincubating GPVI with collagen before adding the mixture to the platelet suspension, aggregation could is be inhibited in a dose-dependant manner. These platelets still aggregated when fresh collagen was added. Under non-reducing conditions, the isolated protein has a Mr of 62 kDa with a shift toward a slightly higher Mr (65 kDa) under reducing conditions. As the amino terminus of GPVI was found to be blocked, the protein was digested with the enzymes LysC and LysC/AspN which produced 4 and 6 peptides, respectively, from which sequence was obtained. The peptides were separated by reverse phase HPLC on a C4 column and sequenced using the Edman method. The amino acid sequences of these peptides are underlined in the translated cDNA sequence (FIG. 1).

I claim:

1. A method of screening for an inhibitor of glycoprotein VI (GPVI)—collagen interaction, comprising
   binding recombinant glycoprotein VI polypeptide (GPVI) comprising a polypeptide sequence encoded by the nucleic acid sequence of SEQ ID NO: 1 or a fragment thereof comprising the extracellular domain of said polypeptide sequence and collagen in the presence of a potential inhibitor in a binding assay,
   wherein reduction of said binding in the presence of said potential inhibitor as compared to said binding in the absence of said potential inhibitor indicates the presence of an inhibitor.

2. The method according to claim 1, wherein said glycoprotein VI polypeptide comprises the polypeptide sequence of SEQ ID NO: 3 or a fragment thereof comprising the extracellular domain of said SEQ ID NO: 3.

* * * * *

SEQUENCE LISTING

```
<160> NUMBER OF SEQ ID NOS: 11

<210> SEQ ID NO 1
<211> LENGTH: 1249
<212> TYPE: DNA
<213> ORGANISM: Homo sapiens
<220> FEATURE:
<221> NAME/KEY: CDS
<222> LOCATION: (26)..(85)
<223> OTHER INFORMATION: Leader sequence
<220> FEATURE:
<221> NAME/KEY: CDS
<222> LOCATION: (86)..(1042)
<223> OTHER INFORMATION: mature GPVI protein

<400> SEQUENCE: 1
gagctcagga cagggctgag gaacc atg tct cca tcc ccg acc gcc ctc ttc      52
                           Met Ser Pro Ser Pro Thr Ala Leu Phe
                           1               5 tgt ctt ggg ctg tgt ctg ggg cgt gtg cca gcg cag agt gga ccg ctc     100
Cys Leu Gly Leu Cys Leu Gly Arg Val Pro Ala Gln Ser Gly Pro Leu
 10              15                  20                  25
```

-continued

| | |
|---|---|
| ccc aag ccc tcc ctc cag gct ctg ccc agc tcc ctg gtg ccc ctg gag<br>Pro Lys Pro Ser Leu Gln Ala Leu Pro Ser Ser Leu Val Pro Leu Glu<br>                   30                       35                      40 | 148 |
| aag cca gtg acc ctc cgg tgc cag gga cct ccg ggc gtg gac ctg tac<br>Lys Pro Val Thr Leu Arg Cys Gln Gly Pro Pro Gly Val Asp Leu Tyr<br>                   45                       50                       55 | 196 |
| cgc ctg gag aag ctg agt tcc agc agg tac cag gat cag gca gtc ctc<br>Arg Leu Glu Lys Leu Ser Ser Ser Arg Tyr Gln Asp Gln Ala Val Leu<br>                60                       65                       70 | 244 |
| ttc atc ccg gcc atg aag aga agt ctg gct gga cgc tac cgc tgc tcc<br>Phe Ile Pro Ala Met Lys Arg Ser Leu Ala Gly Arg Tyr Arg Cys Ser<br> 75                        80                       85 | 292 |
| tac cag aac gga agc ctc tgg tcc ctg ccc agc gac cag ctg gag ctc<br>Tyr Gln Asn Gly Ser Leu Trp Ser Leu Pro Ser Asp Gln Leu Glu Leu<br>90                   95                      100                  105 | 340 |
| gtt gcc acg gga gtt ttt gcc aaa ccc tcg ctc tca gcc cag ccc ggc<br>Val Ala Thr Gly Val Phe Ala Lys Pro Ser Leu Ser Ala Gln Pro Gly<br>                  110                     115                  120 | 388 |
| ccg gcg gtg tcg tca gga ggg gac gta acc cta cag tgt cag act cgg<br>Pro Ala Val Ser Ser Gly Gly Asp Val Thr Leu Gln Cys Gln Thr Arg<br>                 125                     130                  135 | 436 |
| tat ggc ttt gac caa ttt gct ctg tac aag gaa ggg gac cct gcg ccc<br>Tyr Gly Phe Asp Gln Phe Ala Leu Tyr Lys Glu Gly Asp Pro Ala Pro<br>                 140                     145                  150 | 484 |
| tac aag aat ccc gag aga tgg tac cgg gct agt ttc ccc atc atc acg<br>Tyr Lys Asn Pro Glu Arg Trp Tyr Arg Ala Ser Phe Pro Ile Ile Thr<br>         155                     160                     165 | 532 |
| gtg acc gcc gcc cac agc gga acc tac cga tgc tac agc ttc tcc agc<br>Val Thr Ala Ala His Ser Gly Thr Tyr Arg Cys Tyr Ser Phe Ser Ser<br>170                   175                     180                  185 | 580 |
| agg gac cca tac ctg tgg tcg gcc ccc agc gac ccc ctg gag ctt gtg<br>Arg Asp Pro Tyr Leu Trp Ser Ala Pro Ser Asp Pro Leu Glu Leu Val<br>                 190                     195                  200 | 628 |
| gtc aca gga acc tct gtg acc ccc agc cgg tta cca aca gaa cca cct<br>Val Thr Gly Thr Ser Val Thr Pro Ser Arg Leu Pro Thr Glu Pro Pro<br>               205                     210                  215 | 676 |
| tcc tcg gta gca gaa ttc tca gaa gcc acc gct gaa ctg acc gtc tca<br>Ser Ser Val Ala Glu Phe Ser Glu Ala Thr Ala Glu Leu Thr Val Ser<br>               220                     225                  230 | 724 |
| ttc aca aac aaa gtc ttc aca act gag act tct agg agt atc acc acc<br>Phe Thr Asn Lys Val Phe Thr Thr Glu Thr Ser Arg Ser Ile Thr Thr<br>         235                     240                     245 | 772 |
| agt cca aag gag tca gac tct cca gct ggt cct gcc cgc cag tac tac<br>Ser Pro Lys Glu Ser Asp Ser Pro Ala Gly Pro Ala Arg Gln Tyr Tyr<br>250                   255                     260                  265 | 820 |
| acc aag ggc aac ctg gtc cgg ata tgc ctc ggg gct gtg atc cta ata<br>Thr Lys Gly Asn Leu Val Arg Ile Cys Leu Gly Ala Val Ile Leu Ile<br>               270                     275                  280 | 868 |
| atc ctg gcg ggg ttt ctg gca gag gac tgg cac agc cgg agg aag cgc<br>Ile Leu Ala Gly Phe Leu Ala Glu Asp Trp His Ser Arg Arg Lys Arg<br>               285                     290                  295 | 916 |
| ctg cgg cac agg ggc agg gct gtg cag agg ccg ctt ccg ccc ctg ccg<br>Leu Arg His Arg Gly Arg Ala Val Gln Arg Pro Leu Pro Pro Leu Pro<br>               300                     305                  310 | 964 |
| ccc ctc ccg cag acc cgg aaa tca cac ggg ggt cag gat gga ggc cga<br>Pro Leu Pro Gln Thr Arg Lys Ser His Gly Gly Gln Asp Gly Gly Arg<br>               315                     320                  325 | 1012 |
| cag gat gtt cac agc cgc ggg tta tgt tca tgaccgctga accccaggca<br>Gln Asp Val His Ser Arg Gly Leu Cys Ser<br>330                 335 | 1062 |

-continued

```
cggtcgtatc caagggaggg atcatggcat gggaggcgac tcaaagactg gcgtgtgtgg    1122
agcgtggaag caggagggca gaggctacag ctgtggaaac gaggccatgc tgcctcctcc    1182
tggtgttcca tcagggagcc gttcggccag tgtctgtctg tctgtctgcc tctctgtctg    1242
agggcac                                                               1249
```

<210> SEQ ID NO 2
<211> LENGTH: 20
<212> TYPE: PRT
<213> ORGANISM: Homo sapiens

<400> SEQUENCE: 2

Met Ser Pro Ser Pro Thr Ala Leu Phe Cys Leu Gly Leu Cys Leu Gly
1               5                   10                  15

Arg Val Pro Ala
            20

<210> SEQ ID NO 3
<211> LENGTH: 319
<212> TYPE: PRT
<213> ORGANISM: Homo sapiens

<400> SEQUENCE: 3

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
                20                  25                  30

Gly Val Asp Leu Tyr Arg Leu Glu Lys Leu Ser Ser Ser Arg Tyr Gln
            35                  40                  45

Asp Gln Ala Val Leu Phe Ile Pro Ala Met Lys Arg Ser Leu Ala Gly
        50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
                100                 105                 110

Gln Cys Gln Thr Arg Tyr Gly Phe Asp Gln Phe Ala Leu Tyr Lys Glu
            115                 120                 125

Gly Asp Pro Ala Pro Tyr Lys Asn Pro Glu Arg Trp Tyr Arg Ala Ser
        130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Leu Val Arg Ile Cys Leu Gly
                245                 250                 255

Ala Val Ile Leu Ile Ile Leu Ala Gly Phe Leu Ala Glu Asp Trp His

```
                      260                 265                 270
Ser Arg Arg Lys Arg Leu Arg His Arg Gly Arg Ala Val Gln Arg Pro
            275                 280                 285

Leu Pro Pro Leu Pro Pro Leu Pro Gln Thr Arg Lys Ser His Gly Gly
        290                 295                 300

Gln Asp Gly Gly Arg Gln Asp Val His Ser Arg Gly Leu Cys Ser
305                 310                 315

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:  Synthetic
      degenerate primer
<220> FEATURE:
<221> NAME/KEY: modified_base
<222> LOCATION: (8)..(8)
<223> OTHER INFORMATION: a, t, c, g, other or unknown
<220> FEATURE:
<221> NAME/KEY: modified_base
<222> LOCATION: (11)..(11)
<223> OTHER INFORMATION: a, t, c, g, other or unknown

<400> SEQUENCE: 4
tyathccngc natgaarmg                                                    19

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Ala Met Lys Arg Ser Leu
1               5

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:  Synthetic
      degenerate primer
<220> FEATURE:
<221> NAME/KEY: modified_base
<222> LOCATION: (6)..(6)
<223> OTHER INFORMATION: a, t, c, g, other or unknown
<220> FEATURE:
<221> NAME/KEY: modified_base
<222> LOCATION: (9)..(9)
<223> OTHER INFORMATION: a, t, c, g, other or unknown

<400> SEQUENCE: 6
ttrtanarng craaytgrtc                                                   20

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Gln Phe Ala Leu Tyr Lys
1               5
```

```
<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgaatgagac ggtcagttca gc                                              22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttgtacagag caaattggtc                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaccagaggc ttccgttctg                                                 20

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Gln Leu Glu Leu Val Ala Thr Gly Val Phe Ala Lys Pro Ser Leu
1               5                   10                  15

Ser Ala Gln Pro Gly Pro Ala Val Ser Ser
            20                  25
```